US007550407B2

United States Patent
Bartsch et al.

(10) Patent No.: US 7,550,407 B2
(45) Date of Patent: *Jun. 23, 2009

(54) SYSTEM SUITABLE FOR THE HYDROCYANATION OF OLEFINICALLY UNSATURATED COMPOUNDS

(75) Inventors: Michael Bartsch, Neustadt (DE); Robert Baumann, Mannheim (DE); Gerd Haderlein, Grünstadt (DE); Miquel Angel Flores, Aranjuez (ES); Tim Jungkamp, Sandhausen (DE); Hermann Luyken, Ludwigshafen (DE); Jens Scheidel, Hirschberg (DE); Wolfgang Siegel, Limburgerhof (DE); Ferenc Molnar, Speyer (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 294 days.

This patent is subject to a terminal disclaimer.

(21) Appl. No.: 10/551,139

(22) PCT Filed: Mar. 24, 2004

(86) PCT No.: PCT/EP2004/003103

§ 371 (c)(1), (2), (4) Date: Sep. 29, 2005

(87) PCT Pub. No.: WO2004/087314

PCT Pub. Date: Oct. 14, 2004

(65) Prior Publication Data

US 2006/0258874 A1    Nov. 16, 2006

(30) Foreign Application Priority Data

Mar. 31, 2003   (DE) ................ 103 14 761

(51) Int. Cl.
*B01J 31/00* (2006.01)
*C07F 9/02* (2006.01)

(52) U.S. Cl. ....................... 502/162; 558/155

(58) Field of Classification Search ............... 558/155; 502/162

See application file for complete search history.

(56) References Cited

U.S. PATENT DOCUMENTS

| | | | |
|---|---|---|---|
| 3,496,217 A | 2/1970 | Drinkard, Jr. et al. | |
| 3,496,218 A | 2/1970 | Drinkard, Jr. et al. | |
| 3,565,967 A | 2/1971 | Collette et al. | |
| 4,025,570 A | 5/1977 | Cramer | |
| 4,705,881 A | 11/1987 | Rapoport | |
| 4,774,353 A | 9/1988 | Hall et al. | |
| 4,874,884 A | 10/1989 | McKinney et al. | |
| 5,169,971 A | 12/1992 | Inomata et al. | |
| 5,773,637 A | 6/1998 | Cicha et al. | |
| 6,127,567 A | 10/2000 | Garner et al. | |
| 6,171,996 B1 | 1/2001 | Garner et al. | |
| 6,380,421 B1 | 4/2002 | Lu et al. | |
| 7,084,293 B2 * | 8/2006 | Rosier et al. | ........... 558/335 |

FOREIGN PATENT DOCUMENTS

EP   0 268 448   5/1988

OTHER PUBLICATIONS

Jun et al, 2002, CAS:136:342540.*
International Search Report dated Jul. 27, 2004.

* cited by examiner

*Primary Examiner*—Rei-tsang Shiao
(74) *Attorney, Agent, or Firm*—Connolly Bove Lodge & Hutz LLP

(57) ABSTRACT

A system which is suitable as a catalyst for the hydrocyanation of olefinically unsaturated compounds and comprises
a) Ni(0)
b) a compound which complexes Ni(0) as a ligand and contains trivalent phosphorus,
c) a Lewis acid
and
d) a compound of the formula $M R_n$
where
M: Al or Ti
R: identical or different monovalent alkoxy radicals, in which case a plurality of alkoxy radicals may be bonded together, and additionally, in the case that M=Al, R may be identical or different monovalent alkyl radicals, in which case a plurality of alkyl radicals may be bonded together or one or more alkyl radicals may be bonded to one or more of the abovementioned alkoxy radicals,
n: valency of M,
and processes for hydrocyanating an olefinically unsaturated compound in the presence of such a system.

14 Claims, No Drawings

SYSTEM SUITABLE FOR THE HYDROCYANATION OF OLEFINICALLY UNSATURATED COMPOUNDS

This application claims priority from PCT Application No. PCT/EP2004/003103 filed Mar. 24, 2004 and German Application Ser. No. 10314761.6 filed Mar. 31, 2003, the disclosures of each application are incorporated herein by reference.

The present invention relates to a system which is suitable as a catalyst for the hydrocyanation of olefinically unsaturated compounds and comprises a) Ni(0)
b) a compound which complexes Ni(0) as a ligand and contains trivalent phosphorus,
c) a Lewis acid and d) a compound of the formula $M R_n$ where
M: Al or Ti
R: identical or different monovalent alkoxy radicals, in which case a plurality of alkoxy radicals may be bonded together, and additionally, in the case that M=Al, R may be identical or different monovalent alkyl radicals, in which case a plurality of alkyl radicals may be bonded together or one or more alkyl radicals may be bonded to one or more of the abovementioned alkoxy radicals,
n: valency of M.

In addition, it relates to a process for hydrocyanating an olefinically unsaturated compound in the presence of such a system.

Processes for hydrocyanating an olefinically unsaturated nitrile, in particular the preparation of adipodinitrile by hydrocyanating an olefinically unsaturated compound such as 2-cis-pentenenitrile, 2-trans-pentenenitrile, 3-cis-pentenenitrile, 3-trans-pentenenitrile, 4-pentenenitrile, E-2-methyl-2-butenenitrile, Z-2-methyl-2-butenenitrile, 2-methyl-3-butenenitrile or mixtures thereof, in the presence of a catalyst system comprising a Lewis acid and a complex containing a phosphorus compound suitable as a ligand, such as a monodentate, preferably multidentate, in particular bidentate, compound which coordinates to a central atom via a phosphorus atom which may be present as a phosphine, phosphite, phosphonite or phosphinite or mixture thereof, and a central atom, preferably nickel, cobalt or palladium, in particular nickel, more preferably in the form of nickel (0), are known, for example from U.S. Pat. No. 3,496,217, U.S. Pat. No. 3,496,218, U.S. Pat. No. 4,705,881, U.S. Pat. No. 4,774,353, U.S. Pat. No. 4,874,884, U.S. Pat. No. 5,773,637, U.S. Pat. No. 6,127,567, U.S. Pat. No. 6,171,996 B1 and U.S. Pat. No. 6,380,421 B1.

It is an object of the present invention to provide a system which is suitable as a catalyst for the hydrocyanation of olefinically unsaturated compounds and exhibits an improved space-time yield of hydrocyanation products compared to the known systems.

We have found that this object is achieved by the system defined at the outset and by a process for hydrocyanating an olefinically unsaturated compound in the presence of such a system.

The preparation of Ni(0)-containing catalyst systems is known per se and, for the purposes of the present invention, can be effected by processes known per se.

The system also additionally comprises a compound which is suitable as a ligand for Ni(0) and contains at least one trivalent phosphorus atom, or a mixture of such compounds.

In a preferred embodiment, the compound used as a ligand may be one of the formula $$P(X^1R^1)(X^2R^2)(X^3R^3) \quad (I).$$

In the context of the present invention, this compound is a single compound or a mixture of different compounds of the aforementioned formula.

$X^1, X^2, X^3$ may each independently be oxygen or a single bond.

When all of the $X^1, X^2$ and $X^3$ groups are single bonds, compound (I) is a phosphine of the formula $P(R^1 R^2 R^3)$ with the definitions of $R^1, R^2$ and $R^3$ specified in this description.

When two of the $X^1, X^2$ and $X^3$ groups are single bonds and one is oxygen, compound (I) is a phosphinite of the formula $P(OR^1)(R^2)(R^3)$ or $P(R^1)(OR^2)(R^3)$ or $P(R^1)(R^2)(OR^3)$ with the definitions of $R^1, R^2$ and $R^3$ specified in this description.

When one of the $X^1, X^2$ and $X^3$ groups is a single bond and two are oxygen, compound (I) is a phosphonite of the formula $P(OR^1)(OR^2)(R^3)$ or $P(R^1)(OR^2)(OR^3)$ or $P(OR^1)(R^2)(OR^3)$ with the definitions of $R^1, R^2$ and $R^3$ specified in this description.

In a preferred embodiment, all of the $X^1, X^2$ and $X^3$ groups should be oxygen, so that compound (I) is advantageously a phosphite of the formula $P(OR^1)(OR^2)(OR^3)$ with the definitions of $R^1, R^2$ and $R^3$ specified in this description.

According to the invention, $R^1, R^2, R^3$ are each independently identical or different organic radicals.

$R^1, R^2$ and $R^3$ are each independently alkyl radicals, advantageously having from 1 to 10 carbon atoms, such as methyl, ethyl, n-propyl, i-propyl, n-butyl, i-butyl, s-butyl, t-butyl, aryl groups such as phenyl, o-tolyl, m-tolyl, p-tolyl, 1-naphthyl, 2-naphthyl, or hydrocarbyl, advantageously having from 1 to 20 carbon atoms, such as 1,1'-biphenol, 1,1'-binaphthol.

The $R^1, R^2$ and $R^3$ groups may be bonded together directly, i.e. not solely via the central phosphorus atom. Preference is given to the $R^1, R^2$ and $R^3$ groups not being bonded together directly.

In a preferred embodiment, the $R^1, R^2$ and $R^3$ groups are radicals selected from the group consisting of phenyl, o-tolyl, m-tolyl and p-tolyl.

In a particularly preferred embodiment, a maximum of two of the $R^1, R^2$ and $R^3$ groups should be phenyl groups.

In another preferred embodiment, a maximum of two of the $R^1, R^2$ and $R^3$ groups should be o-tolyl groups.

Particularly preferred compounds which may be used are those of the formula $$(\text{o-tolyl-O}—)_w(\text{m-tolyl-O}—)_x(\text{p-tolyl-O}—)_y(\text{phenyl-O}—)_z P$$

where w, x, y, z are each a natural number
where w+x+y+z=3 and
w, z are each less than or equal to 2, such as (p-tolyl-O—)(phenyl)$_2$P, (m-tolyl-O—)(phenyl)$_2$P, (o-tolyl-O—)(phenyl)$_2$P, (p-tolyl-O—)$_2$(phenyl)P, (m-tolyl-O—)$_2$(phenyl)P, (o-tolyl-O—)$_2$(phenyl)P, (m-tolyl-O—)(p-tolyl-O—)(phenyl)P, (o-tolyl-O—)(p-tolyl-O—)(phenyl)P, (o-tolyl-O—)(m-tolyl-O—)(phenyl)P, (p-tolyl-O—)$_3$P, (m-tolyl-O—)(p-tolyl-O—)$_2$P, (o-tolyl-O—)(p-tolyl-O—)$_2$P, (m-tolyl-O—)$_2$(p-tolyl-O—)P, (o-tolyl-O—)$_2$(p-tolyl-O—)P, (o-tolyl-O—)(m-tolyl-O—)(p-tolyl-O—)P, (m-tolyl-O—)$_3$P, (o-tolyl-O—)(m-tolyl-O—)$_2$P, (o-tolyl-O—)$_2$(m-tolyl-O—)P or mixtures of such compounds.

For example, mixtures comprising (m-tolyl-O—)$_3$P, (m-tolyl-O—)$_2$(p-tolyl-O—)P, (m-tolyl-O—)(p-tolyl-O—)$_2$P and (p-tolyl-O—)$_3$P may be obtained by reacting a mixture comprising m-cresol and p-cresol, in particular in a molar ratio of 2:1, as obtained in the distillative workup of crude oil, with a phosphorus trihalide, such as phosphorus trichloride.

Such compounds and their preparation are known per se.

In a further preferred embodiment, the compound suitable as a ligand for Ni(0) which is used may be one of the formula

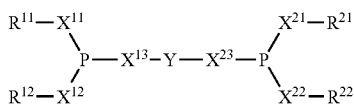

where $X^{11}, X^{12}, X^{13}, X^{21}, X^{22}, X^{23}$ are each independently oxygen or a single bond, $R^{11}, R^{12}$ are each independently identical or different, individual or bridged organic radicals $R^{21}, R^{22}$ are each independently identical or different, individual or bridged organic radicals, Y is a bridging group.

In the context of the present invention, such a compound is a single compound or a mixture of different compounds of the aforementioned formula.

In a preferred embodiment, $X^{11}, X^{12}, X^{13}, X^{21}, X^{22}, X^{23}$ may each be oxygen. In such a case, the bridging group Y is bonded to phosphite groups.

In another preferred embodiment, $X^{11}$ and $X^{12}$ may each be oxygen and $X^{13}$ a single bond, or $X^{11}$ and $X^{13}$ oxygen and $X^{12}$ a single bond, so that the phosphorus atom surrounded by $X^{11}, X^{12}$ and $X^{13}$ is the central atom of a phosphonite. In such a case, $X^{21}, X^{22}$ and $X^{23}$ may be oxygen, or $X^{21}$ and $X^{22}$ may each be oxygen and $X^{23}$ a single bond, or $X^{21}$ and $X^{23}$ may each be oxygen and $X^{22}$ a single bond, or $X^{23}$ may be oxygen and $X^{21}$ and $X^{22}$ each a single bond, or $X^{21}$ may be oxygen and $X^{22}$ and $X^{23}$ each a single bond, or $X^{21}, X^{22}$ and $X^{23}$ may each be a single bond, so that the phosphorus atom surrounded by $X^{21}, X^{22}$ and $X^{23}$ may be the central atom of a phosphite, phosphonite, phosphinite or phosphine, preferably a phosphonite.

In another preferred embodiment, $X^{13}$ may be oxygen and $X^{11}$ and $X^{12}$ each a single bond, or $X^{11}$ may be oxygen and $X^{12}$ and $X^{13}$ each a single bond, so that the phosphorus atom surrounded by $X^{11}, X^{12}$ and $X^{13}$ is the central atom of a phosphinite. In such a case, $X^{21}, X^{22}$ and $X^{23}$ may each be oxygen, or $X^{23}$ may be oxygen and $X^{21}$ and $X^{22}$ a single bond, or $X^{21}$ may be oxygen and $X^{22}$ and $X^{23}$ each a single bond, or $X^{21}, X^{22}$ and $X^{23}$ may each be a single bond, so that the phosphorus atom surrounded by $X^{21}, X^{22}$ and $X^{23}$ may be the central atom of a phosphite, phosphinite or phosphine, preferably a phosphinite.

In another preferred embodiment, $X^{11}, X^{12}$ and $X^{13}$ may each be a single bond, so that the phosphorus atom surrounded by $X^{11}, X^{12}$ and $X^{13}$ is the central atom of a phosphine. In such a case, $X^{21}, X^{22}$ and $X^{23}$ may each be oxygen, or $X^{21}, X^{22}$ and $X^{23}$ may each be a single bond, so that the phosphorus atom surrounded by $X^{21}, X^{22}$ and $X^{23}$ may be the central atom of a phosphite or phosphine, preferably a phosphine.

The bridging group Y is advantageously an aryl group which is substituted, for example by $C_1$-$C_4$-alkyl, halogen, such as fluorine, chlorine, bromine, halogenated alkyl, such as trifluoromethyl, aryl, such as phenyl, or is unsubstituted, preferably a group having from 6 to 20 carbon atoms in the aromatic system, in particular pyrocatechol, bis(phenol) or bis(naphthol).

The $R^{11}$ and $R^{12}$ radicals may each independently be the same or different organic radicals. Advantageous $R^{11}$ and $R^{12}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{21}$ and $R^{22}$ radicals may each independently be the same or different organic radicals. Advantageous $R^{21}$ and $R^{22}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{11}$ and $R^{12}$ radicals may each be separate or bridged.

The $R^{21}$ and $R^{22}$ radicals may each be separate or bridged.

The $R^{11}, R^{12}, R^{21}$ and $R^{22}$ radicals may each be separate, two may be bridged and two separate, or all four may be bridged, in the manner described.

In a particularly preferred embodiment, useful compounds are those of the formula I, II, III, IV and V specified in U.S. Pat. No. 5,723,641.

In a particularly preferred embodiment, useful compounds are those of the formula I, II, III, IV, V, VI and VII specified in U.S. Pat. No. 5,512,696, in particular the compounds used there in examples 1 to 31.

In a particularly preferred embodiment, useful compounds are those of the formula I, II, III, IV, V, VI, VII, VIII, IX, X, XI, XII, XIII, XIV and XV specified in U.S. Pat. No. 5,821,378, in particular the compounds used there in examples 1 to 73.

In a particularly preferred embodiment, useful compounds are those of the formula I, II, III, IV, V and VI specified in U.S. Pat. No. 5,512,695, in particular the compounds used there in examples 1 to 6.

In a particularly preferred embodiment, useful compounds are those of the formula I, II, III, IV, V, VI, VII, VIII, IX, X, XI, XII, XIII and XIV specified in U.S. Pat. No. 5,981,772, in particular the compounds used there in examples 1 to 66.

In a particularly preferred embodiment, useful compounds are those specified in U.S. Pat. No. 6,127,567 and the compounds used there in examples 1 to 29.

In a particularly preferred embodiment, useful compounds are those of the formula I, II, III, IV, V, VI, VII, VIII, IX and X specified in U.S. Pat. No. 6,020,516, in particular the compounds used there in examples 1 to 33.

In a particularly preferred embodiment, useful compounds are those specified in U.S. Pat. No. 5,959,135, and the compounds used there in examples 1 to 13.

In a particularly preferred embodiment, useful compounds are those of the formula I, II, and III specified in U.S. Pat. No. 5,847,191.

In a particularly preferred embodiment, useful compounds are those specified in U.S. Pat. No. 5,523,453, in particular the compounds illustrated there in formula 1, 2, 3, 4, 5, 6, 7, 8, 9, 10, 11, 12, 13, 14, 15, 16, 17, 18, 19, 20 and 21.

In a particularly preferred embodiment, useful compounds are those specified in WO 01/14392, preferably the compounds illustrated there in formula V, VI, VII, VIII, IX, X, XI, XII, XIII, XIV, XV, XVI, XVII, XXI, XXII, XXIII.

In a particularly preferred embodiment, useful compounds are those specified in WO 98/27054.

In a particularly preferred embodiment, useful compounds are those specified in WO 99/13983.

In a particularly preferred embodiment, useful compounds are those specified in WO 99/64155.

In a particularly preferred embodiment, useful compounds are those specified in the German laid-open specification DE 10038037.

In a particularly preferred embodiment, useful compounds are those specified in the German laid-open specification DE 10046025.

Such compounds and their preparation are known per se.

In a further preferred embodiment, a mixture of one or more of the aforementioned compounds which are suitable as a ligand for Ni(0) and contain one phosphorus atom, and one or more compounds which are suitable as a ligand for Ni(0) and contain two phosphorus atoms may be used.

In this case, the ratio of the first component to the second component may be in the range from 4/1 to 1/1 mol/mol.

In a particularly preferred embodiment, useful systems are those which are specified in the international patent application PCT/EP02/07888 and comprise Ni(0) and such mixtures.

In addition, the system comprises a Lewis acid.

In the context of the present invention, a Lewis acid is either a single Lewis acid or else a mixture of a plurality of, for example two, three or four, Lewis acids.

Useful Lewis acids are inorganic or organic metal compounds in which the cation is selected from the group consisting of scandium, titanium, vanadium, chromium, manganese, iron, cobalt, copper, zinc, boron, aluminum, yttrium, zirconium, niobium, molybdenum, cadmium, rhenium and tin. Examples include $ZnBr_2$, $ZnI_2$, $ZnCl_2$, $ZnSO_4$, $CuCl_2$, CuCl, $Cu(O_3SCF_3)_2$, $CoCl_2$, $CoI_2$, $FeI_2$, $FeCl_3$, $FeCl_2$, $FeCl_2(THF)_2$, $TiCl_4(THF)_2$, $TiCl_4$, $TiCl_3$, $ClTi(O-i-propyl)_3$, $MnCl_2$, $ScCl_3$, $AlCl_3$, $(C_8H_{17})AlCl_2$, $(C_8H_{17})_2AlCl$, $(i-C_4H_9)_2 AlCl$, $(C_6H_5)_2AlCl$, $(C_6H_5)AlCl_2$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $B(C_6H_5)_3$, $TaCl_5$, as described, for example, in U.S. Pat. No. 6,127,567, U.S. Pat. No. 6,171,996 and U.S. Pat. No. 6,380,421. Also useful are metal salts such as $ZnCl_2$, $CoI_2$ and $SnCl_2$, and organometallic compounds such as $RAlCl_2$, $R_2AlCl$, $RSnO_3SCF_3$ and $R_3B$, where R is an alkyl or aryl group, as described, for example, in U.S. Pat. No. 3,496,217, U.S. Pat. No. 3,496,218 and U.S. Pat. No. 4,774,353. According to U.S. Pat. No. 3,773,809, the promoter used may also be a metal in cationic form which is selected from the group consisting of zinc, cadmium, beryllium, aluminum, gallium, indium, thallium, titanium, zirconium, hafnium, erbium, germanium, tin, vanadium, niobium, scandium, chromium, molybdenum, tungsten, manganese, rhenium, palladium, thorium, iron and cobalt, preferably zinc, cadmium, titanium, tin, chromium, iron, aluminium and cobalt, and the anionic moiety of the compound may be selected from the group consisting of halides such as fluoride, chloride, bromide and iodide, anions of lower fatty acids having from 2 to 7 carbon atoms, $HPO_3^{2-}$, $H_3PO^{2-}$, $CF_3COO^-$, $C_7H_{15}OSO_2^-$ or $SO_4^{2-}$. Further suitable promoters disclosed by U.S. Pat. No. 3,773,809 are borohydrides, organoborohydrides and boric esters of the formula $R_3B$ and $B(OR)_3$, where R is selected from the group consisting of hydrogen, aryl radicals having from 6 to 18 carbon atoms, aryl radicals substituted by alkyl groups having from 1 to 7 carbon atoms and aryl radicals substituted by cyano-substituted alkyl groups having from 1 to 7 carbon atoms, advantageously triphenylboron. Moreover, as described in U.S. Pat. No. 4,874,884, it is possible to use synergistically active combinations of Lewis acids, in order to increase the activity of the catalyst system. Suitable promoters may, for example, be selected from the group consisting of $CdCl_2$, $FeCl_2$, $ZnCl_2$, $B(C_6H_5)_3$ and $(C_6H_5)_3SnX$, where $X=CF_3SO_3$, $CH_3C_6H_4SO_3$ or $(C_6H_5)_3BCN$, and the preferred ratio specified of promoter to nickel is from about 1:16 to about 50:1.

In the context of the present invention, the term Lewis acid also includes the promoters specified in U.S. Pat. No. 3,496,217, U.S. Pat. No. 3,496,218, U.S. Pat. No. 4,774,353, U.S. Pat. No. 4,874,884, U.S. Pat. No. 6,127,567, U.S. Pat. No. 6,171,996 and U.S. Pat. No. 6,380,421.

Particularly preferred Lewis acids among those mentioned are in particular metal salts, more preferably metal halides, such as fluorides, chlorides, bromides, iodides, in particular chlorides, of which particular preference is given to zinc chloride, iron(II) chloride and iron(III) chloride.

According to the invention, the system comprises a compound d) of the formula $M R_n$ where M: Al or Ti R: identical or different monovalent alkoxy radicals, in which case a plurality of alkoxy radicals may be bonded together, and additionally, in the case that M=Al, R may be identical or different monovalent alkyl radicals, in which case a plurality of alkyl radicals may be bonded together or one or more alkyl radicals may be bonded to one or more of the abovementioned alkoxy radicals, n: valency of M.

In the context of the present invention, a compound d) may be a single compound or else a mixture of different compounds of this type, and the different compounds may differ in the nature of M, the nature of R or both.

According to the invention, M is aluminum or titanium, and the valency n of aluminum in compound d) should advantageously be three and the valency n of titanium in compound d) should advantageously be three or four, in particular four. In the context of the definition of n, the valency refers to the number of R radicals on M, irrespective of the oxidation number of M which can be calculated for the particular structure $M R_n$ in compound d).

In the case that M is titanium, R is identical or different, preferably identical, monovalent alkoxy radicals, in which case a plurality of alkoxy radicals may be bonded together, preferably $C_1$-$C_4$-alkoxy radicals, such as methoxy, ethoxy, 1-propoxy, 2-propoxy, 1-n-butoxy, 2-n-butoxy, 1-isobutoxy or 2-isobutoxy, preferably $Ti(OMe)_4$, $Ti(OEt)_4$, $Ti(O-i-Pr)_4$, $Ti(O-n-Pr)_4$, in particular $Ti(O-i-Pr)_4$.

In a preferred embodiment, compound d) may be a titanium tetraalkoxide, in particular $Ti(O-i-Pr)_4$.

In the case that M is aluminum, R is identical or different, preferably identical, monovalent alkoxy radicals, in which case a plurality of alkoxy radicals may be bonded together, preferably $C_1$-$C_4$-alkoxy radicals, such as methoxy, ethoxy, 1-propoxy, 2-propoxy, 1-n-butoxy, 2-n-butoxy, 1-isobutoxy or 2-isobutoxy, preferably $Al(OMe)_3$, $Al(OEt)_3$, $Al(O-i-Pr)_3$, $Al(O-s-Bu)_3$, in particular $Al(O-s-Bu)_3$ or identical or different, preferably identical, monovalent alkyl radicals, in which case a plurality of alkyl radicals may be bonded together or one or more alkyl radicals may be bonded to one or more of the abovementioned alkoxy radicals, preferably $C_1$-$C_4$-alkyl radicals such as methyl, ethyl, 1-propyl, 2-propyl, 1-n-butyl, 2-n-butyl, 1-isobutyl or 2-isobutyl, preferably $Me_3Al$, $Et_3Al$, $i-Pr_3Al$, $Bu_3Al$, in particular $Et_3Al$, or such mixed alkoxyalkyl radicals.

In a preferred embodiment, compound d) may be an aluminum trialkoxide, in particular $Al(O-s-Bu)_3$.

In a further preferred embodiment, compound d) may be a trialkylaluminum, in particular $Et_3Al$.

Advantageously, compound d), based on Ni, may be used in amounts of from 0.01 to 2, preferably from 0.01 to 1.5, in particular from 0.01 to 1 mol/mol (w/w).

The preparation of catalyst systems comprising the components a), b) and c) is known per se; the system according to the invention can be prepared in accordance with these known processes.

In processes for hydrocyanating olefinically unsaturated compounds in the presence of Ni(0)-containing catalyst systems, it is advantageous in accordance with the invention to use the present systems comprising compounds a), b), c) and d) as Ni(0)-containing catalysts.

In the context of the present invention, olefinically unsaturated compound refers either to a single olefinically unsaturated compound or to a mixture of such olefinically unsaturated compounds.

Useful olefinically unsaturated compounds are compounds which have one or more, such as two, three or four, preferably one or two, in particular one, carbon-carbon double bonds. The olefinically unsaturated compounds may advantageously be a branched or unbranched alkene, preferably having from 2 to 10 carbon atoms, or an arylalkene, such as a monoarylalkene or bisarylalkene, preferably having from 2 to 10 carbon atoms in the alkene backbone.

Such olefinically unsaturated compounds may be unsubstituted.

In a preferred embodiment, a substituted olefinically unsaturated compound is used, preferably an olefinically unsaturated compound which contains a functional group selected from the group consisting of —CN, —COOR$^{31}$, —CONR$^{32}$R$^{33}$ where R$^{31}$, R$^{32}$, R$^{33}$: each independently, in the case that R$^{32}$ and R$^{33}$ are the same or different, H or alkyl, preferably C$_1$-C$_4$-alkyl, such as methyl, ethyl, 1-propyl, 2-propyl, 1-n-butyl, 2-n-butyl, 1-isobutyl or 2-isobutyl.

In a further preferred embodiment, the substituted olefinically unsaturated compound used may be a compound of the formula (C$_4$H$_7$)-X where X: functional group selected from the group consisting of —CN, —COOR$^{41}$, —CONR$^{42}$R$^{43}$ where R$^{41}$, R$^{42}$, R$^{43}$: each independently, in the case that R$^{42}$ and R$^{43}$ are the same or different, H or alkyl, preferably C$_1$-C$_4$-alkyl, such as methyl, ethyl, 1-propyl, 2-propyl, 1-n-butyl, 2-n-butyl, 1-isobutyl or 2-isobutyl.

In a further preferred embodiment, the olefinically unsaturated compound used may be a branched, preferably linear, pentenenitrile, such as 2-cis-pentenenitrile, 2-trans-pentenenitrile, 3-cis-pentenenitrile, 3-trans-pentenenitrile, 4-pentenenitrile, E-2-methyl-2-butenenitrile, Z-2-methyl-2-butenenitrile, 2-methyl-3-butenenitrile or mixtures thereof.

In a particularly preferred embodiment, the olefinically unsaturated compound used is 3-pentenenitrile, such as 3-cis-pentenenitrile or 3-trans-pentenenitrile, 4-pentenenitrile or mixtures thereof.

Such pentenenitriles can be obtained by processes known per se, for example by hydrocyanation of butadiene in the presnce of Ni(0)-containing catalysts.

Processes for hydrocyanating olefinically unsaturated compounds in the presence of Ni(0)-containing catalyst systems are known per se. The processes according to the invention can be carried out in accordance with these processes known per se.

The adiponitrile ("ADN") obtainable as a product in such a hydrocyanation or the compounds obtainable by hydrogenating ADN, 6-aminocapronitrile ("ACN") and hexamethylenediamine ("HMD") can be used to prepare polyamides, in particular nylon-6 and nylon-6,6.

The invention is illustrated by the nonlimiting examples which follow.

EXAMPLES

All examples and comparative examples were carried out in an argon protective gas atmosphere.

Nickel(0)(m-/p-tolyl phosphite)$_{5-7}$ ("NTP") is a solution of 2.35% by weight of nickel(0) with 19% by weight of 3-pentenenitrile ("3PN") and 78.65% by weight of m-/p-tolyl phosphite with an m/p ratio of 2:1.

The ligands used were:

Ligand 1

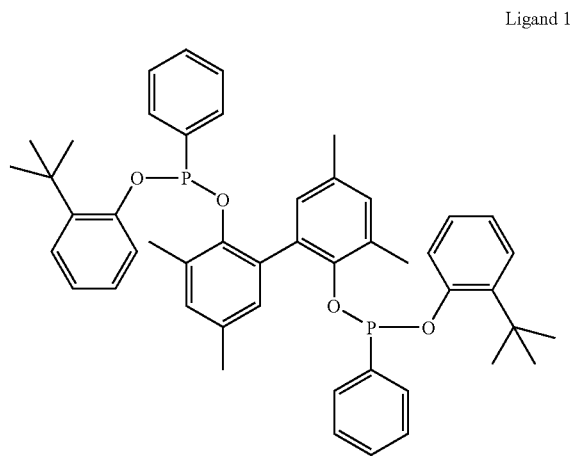

Ligand 2

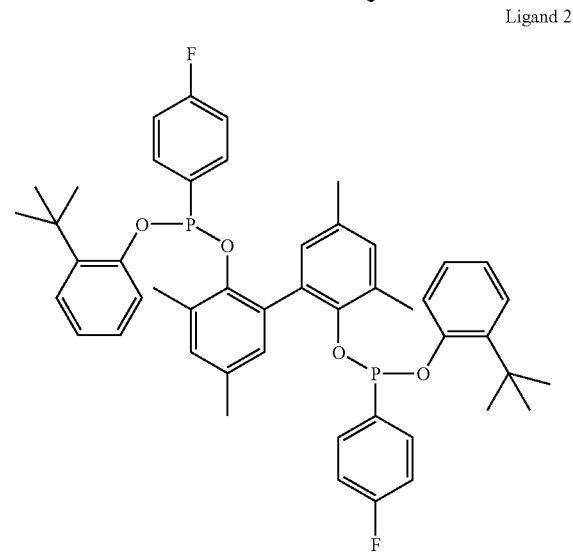

Ligand 3

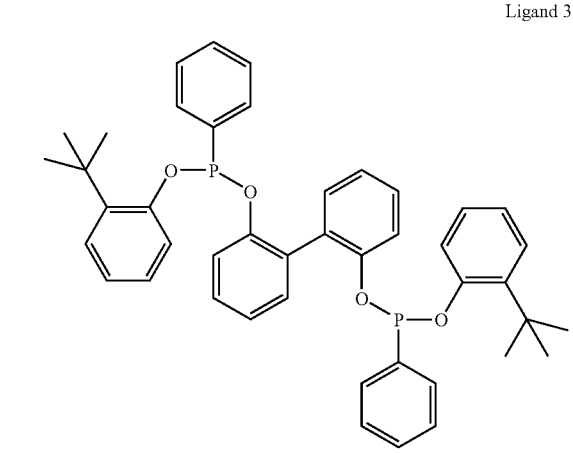

-continued

Ligand 4

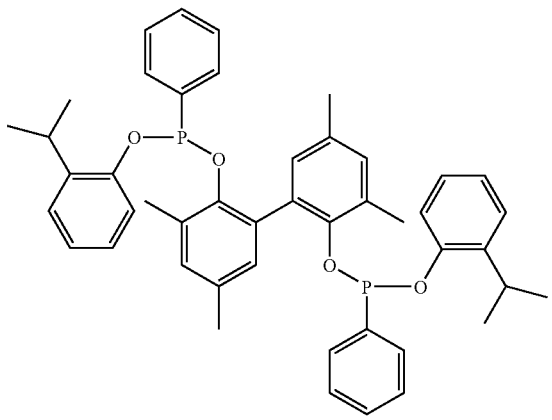

Ligand 5

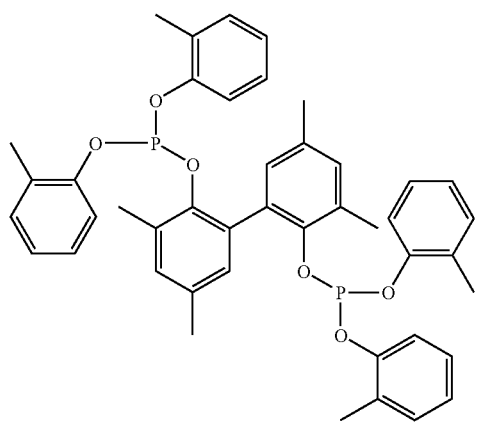

Ligand 6

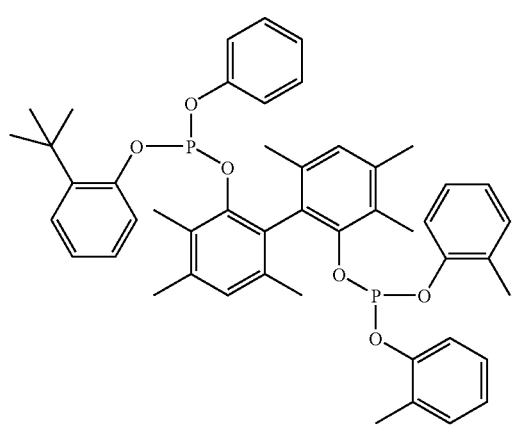

In addition, "ADN" means adiponitrile, "4PN" means 4-pentenenitrile and "Ni(COD)$_2$" means Ni(0)-bis(cyclooctadiene) complex.

Hydrocyanation of 3PN to ADN

Example 1 (Comparative), (0.42 mmol of Ni(0))

1 eq. of NTP was admixed with 1000 eq. of 3PN and 2 eq. of ligand 1, stirred at 25° C. for one hour and heated to 73° C. In an Ar carrier gas stream, 277 eq. of HCN/h*Ni were then injected. After 10 min., the mixture took up no more HCN; a sample was taken from the reaction mixture and the following results were obtained by gas chromatography (GC percent by weight, internal standard: ethylbenzene):

| 4PN | MGN | ADN | ADN selectivity (%) |
|---|---|---|---|
| 5.0 | 0.1 | 1.2 | 94.0 |

Example 2 (Comparative) (0.42 mmol of Ni(0))

1 eq. of NTP was admixed with 1000 eq. of 3PN and 2 eq. of ligand 1, stirred at 25° C. for one hour and heated to 73° C. 1 eq. of Et$_3$Al was added to this mixture and it was stirred for a further 5 min. In an Ar carrier gas stream, 276 eq. of HCN/h*Ni were then injected. After 20 min., the mixture took up no more HCN; a sample was taken from the reaction mixture and the following results were obtained by gas chromatography (GC percent by weight, internal standard: ethylbenzene):

| 4PN | MGN | ADN | ADN selectivity (%) |
|---|---|---|---|
| 4.8 | 0.1 | 0.9 | 88.0 |

Example 3 (Comparative) (0.42 mmol of Ni(0))

1 eq. of NTP was admixed with 1000 eq. of 3PN and 2 eq. of ligand 1, stirred at 25° C. for one hour and heated to 60° C. 1 eq. of ZnCl$_2$ was added to this mixture and it was stirred for a further 5 min. In an Ar carrier gas stream, 351 eq. of HCN/h*Ni were then injected. After 65 min., the mixture took up no more HCN; a sample was taken from the reaction mixture and the following results were obtained by gas chromatography (GC percent by weight, internal standard: ethylbenzene):

| 4PN | MGN | ADN | ADN selectivity (%) |
|---|---|---|---|
| 2.1 | 2.0 | 35.8 | 94.8 |

Example 4 (Inventive) (0.47 mmol of Ni(0))

1 eq. of NTP was admixed with 1000 eq. of 3PN and 2 eq. of ligand 1, stirred at 25° C. for one hour and heated to 60° C. 1 eq. of Et$_3$Al and 1 eq. of ZnCl$_2$ was added to this mixture and it was stirred for a further 5 min. In an Ar carrier gas stream, 303 eq. of HCN/h*Ni were then injected. After 140 min., the mixture took up no more HCN; a sample was taken from the reaction mixture and the following results were obtained by gas chromatography (GC percent by weight, internal standard: ethylbenzene):

| 4PN | MGN | AND | ADN selectivity (%) |
|---|---|---|---|
| 0.9 | 3.1 | 64.0 | 95.5 |

Example 5 (Comparative): (0.47 mmol of Ni(0))

1 eq. of Ni(COD)$_2$ was admixed with 3 eq. of ligand 1 and 1000 eq. of 3PN, stirred at 25° C. for one hour and heated to 73° C. 1 eq. of ZnCl$_2$ was added to this mixture and it was stirred for a further 5 min. In an Ar carrier gas stream, 271 eq. of HCN/h*Ni were then injected. After 120 min., the mixture took up no more HCN; a sample was taken from the reaction mixture and the following results were obtained by gas chromatography (GC percent by weight, internal standard: ethylbenzene):

| 4PN | MGN | ADN | ADN selectivity (%) |
|---|---|---|---|
| 1.7 | 3.3 | 50.9 | 94.0 |

Example 6 (Inventive) (0.47 mmol of Ni(0))

1 eq. of Ni(COD)$_2$ was admixed with 3 eq. of ligand 1 and 1000 eq. of 3PN, stirred at 25° C. for one hour and heated to 73° C. 1 eq. of Et$_3$Al and 1 eq. of ZnCl$_2$ was added to this mixture and it was stirred for a further 5 min. In an Ar carrier gas stream, 268 eq. of HCN/h*Ni were then injected. After 150 min., the mixture took up no more HCN; a sample was taken from the reaction mixture and the following results were obtained by gas chromatography (GC percent by weight, internal standard: ethylbenzene):

| 4PN | MGN | AND | ADN selectivity (%) |
|---|---|---|---|
| 1.4 | 3.4 | 61.3 | 94.7 |

Example 7 (Comparative): (0.38 mmol of Ni(0))

1 eq. of NTP was admixed with 1000 eq. of 3PN and 2 eq. of ligand 1, stirred at 25° C. for one hour and heated to 73° C. 1 eq. of FeCl$_2$ was added to this mixture and it was stirred for a further 5 min. In an Ar carrier gas stream, 319 eq. of HCN/h*Ni were then injected. After 60 min., the mixture took up no more HCN; a sample was taken from the reaction mixture and the following results were obtained by gas chromatography (GC percent by weight, internal standard: ethylbenzene):

| 4PN | MGN | ADN | ADN selectivity (%) |
|---|---|---|---|
| 2.5 | 2.5 | 31.8 | 92.6 |

Example 8 (Inventive) (0.38 mmol of Ni(0))

1 eq. of NTP was admixed with 1000 eq. of 3PN and 2 eq. of ligand 1, stirred at 25° C. for one hour and heated to 73° C. 0.35 eq. of Et$_3$Al and 1 eq. of FeCl$_2$ was added to this mixture and it was stirred for a further 5 min. In an Ar carrier gas stream, 324 eq. of HCN/h*Ni were then injected. After 110 min., the mixture took up no more HCN; a sample was taken from the reaction mixture and the following results were obtained by gas chromatography (GC percent by weight, internal standard: ethylbenzene):

| 4PN | MGN | AND | ADN selectivity (%) |
|---|---|---|---|
| 1.5 | 3.5 | 50.9 | 93.5 |

Example 9 (Comparative) (0.46 mmol of Ni(0))

1 eq. of Ni(COD)$_2$ was admixed with 3 eq. of ligand 1 and 1000 eq. of 3PN, stirred at 25° C. for one hour and heated to 73° C. 1 eq. of FeCl$_2$ was added to this mixture and it was stirred for a further 5 min. In an Ar carrier gas stream, 256 eq. of HCN/h*Ni were then injected. After 140 min., the mixture took up no more HCN; a sample was taken from the reaction mixture and the following results were obtained by gas chromatography (GC percent by weight, internal standard: ethylbenzene):

| 4PN | MGN | ADN | ADN selectivity (%) |
|---|---|---|---|
| 1.3 | 3.9 | 61.1 | 94.0 |

Example 10 (Inventive) (0.4 mmol of Ni(0))

1 eq. of Ni(COD)$_2$ was admixed with 3 eq. of ligand 1 and 1000 eq. of 3PN, stirred at 25° C. for one hour and heated to 73° C. 0.35 eq. of Et$_3$Al and 1 eq. of FeCl$_2$ was added to this mixture and it was stirred for a further 5 min. In an Ar carrier gas stream, 300 eq. of HCN/h*Ni were then injected. After 150 min., the mixture took up no more HCN; a sample was taken from the reaction mixture and the following results were obtained by gas chromatography (GC percent by weight, internal standard: ethylbenzene):

| 4PN | MGN | AND | ADN selectivity (%) |
|---|---|---|---|
| 1.0 | 4.2 | 69.4 | 94.3 |

Example 11 (Comparative) (0.43 mmol of Ni(0))

1 eq. of NTP was admixed with 1000 eq. of 3PN and 2 eq. of ligand 1, stirred at 25° C. for one hour and heated to 73° C. 10 eq. of Al(O-s-Bu)$_3$ and 1 eq. of FeCl$_2$ was added to this mixture and it was stirred for a further 5 min. In an Ar carrier gas stream, 294 eq. of HCN/h*Ni were then injected. After 15 min., the mixture took up no more HCN; a sample was taken from the reaction mixture and the following results were obtained by gas chromatography (GC percent by weight, internal standard: ethylbenzene):

| 4PN | MGN | ADN | ADN selectivity (%) |
|---|---|---|---|
| 1.6 | 0.1 | 0.2 | — |

Example 12 (Inventive) (0.42 mmol of Ni(0))

1 eq. of NTP was admixed with 1000 eq. of 3PN and 2 eq. of ligand 1, stirred at 25° C. for one hour and heated to 73° C.

0.5 eq. of Al(O-s-Bu)$_3$ and 1 eq. of ZnCl$_2$ was added to this mixture and it was stirred for a further 5 min. In an Ar carrier gas stream, 361 eq. of HCN/h*Ni were then injected. After 80 min., the mixture took up no more HCN; a sample was taken from the reaction mixture and the following results were obtained by gas chromatography (GC percent by weight, internal standard: ethylbenzene):

| 4PN | MGN | AND | ADN selectivity (%) |
|---|---|---|---|
| 1.8 | 3.7 | 51.9 | 93.4 |

Example 13 (Inventive) (0.42 mmol of Ni(0))

1 eq. of NTP was admixed with 1000 eq. of 3PN and 2 eq. of ligand 1, stirred at 25° C. for one hour and heated to 73° C. 1 eq. of Ti(O-Bu)$_4$ and 1 eq. of ZnCl$_2$ was added to this mixture and it was stirred for a further 5 min. In an Ar carrier gas stream, 296 eq. of HCN/h*Ni were then injected. After 100 min., the mixture took up no more HCN; a sample was taken from the reaction mixture and the following results were obtained by gas chromatography (GC percent by weight, internal standard: ethylbenzene):

| 4PN | MGN | AND | ADN selectivity (%) |
|---|---|---|---|
| 2.1 | 3.2 | 48.6 | 93.8 |

Example 14 (Comparative): (0.3 mmol of Ni(0))

1 eq. of NTP was admixed with 300 eq. of 3PN and 2 eq. of ligand 1, stirred at 25° C. for one hour and heated to 70° C. 1 eq. of ZnCl$_2$ was added to this mixture and it was stirred for a further 5 min. In an Ar carrier gas stream, 260 eq. of HCN/h*Ni were then injected. After 1, 2, 3, 4, 5 and 10 minutes, a sample was taken from the reaction mixture and the following results were obtained by gas chromatography (GC percent by weight, internal standard: ethylbenzene):

| Min | 4PN | ADN |
|---|---|---|
| 1 | 2.6 | 3.7 |
| 2 | 3.0 | 7.1 |
| 3 | 3.3 | 9.8 |
| 4 | 3.3 | 12.1 |
| 5 | 3.1 | 15.5 |
| 10 | 2.6 | 27.2 |

Example 15a (Inventive) (0.3 mmol of Ni(0))

1 eq. of NTP was admixed with 300 eq. of 3PN and 2 eq. of ligand 1, stirred at 25° C. for one hour and heated to 70° C. 1 eq. of Et$_3$Al and 1 eq. of ZnCl$_2$ was added to this mixture and it was stirred for a further 5 min. In an Ar carrier gas stream, 260 eq. of HCN/h*Ni were then injected. After 1, 2, 3, 4, 5 and 10 minutes, a sample was taken from the reaction mixture and the following results were obtained by gas chromatography (GC percent by weight, internal standard: ethylbenzene):

| Min | 4PN | ADN |
|---|---|---|
| 1 | 1.9 | 3.6 |
| 2 | 2.2 | 4.5 |
| 3 | 2.4 | 7.7 |
| 4 | 2.6 | 10.9 |
| 5 | 2.6 | 11.5 |
| 10 | 1.5 | 25.4 |

Example 15b (Inventive) (0.3 mmol of Ni(0))

1 eq. of NTP was admixed with 300 eq. of 3PN and 2 eq. of ligand 1, stirred at 25° C. for one hour and heated to 70° C. 1 eq. of Al(O-s-Bu)$_3$ and 1 eq. of ZnCl$_2$ was added to this mixture and it was stirred for a further 5 min. In an Ar carrier gas stream, 265 eq. of HCN/h*Ni were then injected. After 1, 2, 3, 4, 5 and 10 minutes, a sample was taken from the reaction mixture and the following results were obtained by gas chromatography (GC percent by weight, internal standard: ethylbenzene):

| Min | 4PN | ADN |
|---|---|---|
| 1 | 2.7 | 3.2 |
| 2 | 3.1 | 5.2 |
| 3 | 3.3 | 7.8 |
| 4 | 3.4 | 9.6 |
| 5 | 3.3 | 11.9 |
| 10 | 2.5 | 23.9 |

Comparative Overview

| | 4PN content [GC percent by weight] | | |
|---|---|---|---|
| Time [min.] | Example 14 No additive | Example 15a With Et$_3$Al | Example 15b With Al-tri-s-butoxide |
| 1 | 2.6 | 1.9 | 2.7 |
| 2 | 3 | 2.2 | 3.1 |
| 3 | 3.3 | 2.4 | 3.3 |
| 4 | 3.3 | 2.6 | 3.4 |
| 5 | 3.1 | 2.6 | 3.3 |
| 10 | 2.6 | 1.5 | 2.5 |

The inventive additives thus do not exhibit any isomerization activity in the sense of U.S. Pat. No. 4,874,844 within the measurement accuracy.

| | ADN content [GC percent by weight] | | |
|---|---|---|---|
| Time [min.] | Example 14 No additive | Example 15a With Et$_3$Al | Example 15b With Al-tri-s-butoxide |
| 1 | 3.7 | 3.6 | 3.2 |
| 2 | 7.1 | 4.5 | 5.2 |
| 3 | 9.8 | 7.7 | 7.8 |
| 4 | 12.1 | 10.9 | 9.6 |
| 5 | 15.5 | 11.5 | 11.9 |
| 10 | 27.2 | 25.4 | 23.9 |

The inventive additives thus exhibit no influence on the reaction rate of the hydrocyanation in the sense of U.S. Pat. No. 4,874,884 within the measurement accuracy.

Example 16 (Comparative) (0.29 mmol of Ni(0))

1 eq. of NTP was admixed with 1000 eq. of 3PN and 2 eq. of ligand 2, stirred at 25° C. and heated to 60° C. 1 eq. of ZnCl₂ was added to this mixture and it was stirred for a further 5 min. In an Ar carrier gas stream, 314 eq. of HCN/h*Ni were then injected. After 50 min., the mixture took up no more HCN; a sample was taken from the reaction mixture and the following results were obtained by gas chromatography (GC percent by weight, internal standard: ethylbenzene):

| 4PN | MGN | ADN | ADN selectivity (%) |
|-----|-----|-----|---------------------|
| 1.8 | 1.5 | 25.0 | 94.4 |

Example 17 (Inventive): (0.29 mmol of Ni(0))

1 eq. of NTP was admixed with 1000 eq. of 3PN and 2 eq. of ligand 2, stirred at 25° C. for one hour and heated to 60° C. 1 eq. of Et₃Al and 1 eq. of ZnCl₂ were added to this mixture and it was stirred for a further 5 min. In an Ar carrier gas stream, 340 eq. of HCN/h*Ni were then injected. After 135 min., the mixture took up no more HCN; a sample was taken from the reaction mixture and the following results were obtained by gas chromatography (GC percent by weight, internal standard: ethylbenzene):

| 4PN | MGN | AND | ADN selectivity (%) |
|-----|-----|-----|---------------------|
| 0.5 | 3.1 | 70.8 | 95.8 |

Example 18 (Comparative) (0.43 mmol of Ni(0))

1 eq. of NTP was admixed with 1000 eq. of 3PN and 2 eq. of ligand 3, stirred at 25° C. for one hour and heated to 60° C. 1 eq. of ZnCl₂ was added to this mixture and it was stirred for a further 5 min. In an Ar carrier gas stream, 297 eq. of HCN/h*Ni were then injected. After 65 min., the mixture took up no more HCN; a sample was taken from the reaction mixture and the following results were obtained by gas chromatography (GC percent by weight, internal standard: ethylbenzene):

| 4PN | MGN | ADN | ADN selectivity (%) |
|-----|-----|-----|---------------------|
| 2.2 | 3.2 | 27.0 | 89.4 |

Example 19 (Inventive) (0.43 mmol of Ni(0))

1 eq. of NTP was admixed with 1000 eq. of 3PN and 2 eq. of ligand 3, stirred at 25° C. for one hour and heated to 60° C. 1 eq. of Et₃Al and 1 eq. of ZnCl₂ were added to this mixture and it was stirred for a further 5 min. In an Ar carrier gas stream, 335 eq. of HCN/h*Ni were then injected. After 160 min., the mixture took up no more HCN; a sample was taken from the reaction mixture and the following results were obtained by gas chromatography (GC percent by weight, internal standard: ethylbenzene):

| 4PN | MGN | AND | ADN selectivity (%) |
|-----|-----|-----|---------------------|
| 0.6 | 8.5 | 70.8 | 89.3 |

Example 20 (Comparative): (0.22 mmol of Ni(0))

1 eq. of NTP was admixed with 1000 eq. of 3PN and 2 eq. of ligand 4, stirred at 25° C. for one hour and heated to 60° C. 1 eq. of ZnCl₂ was added to this mixture and it was stirred for a further 5 min. In an Ar carrier gas stream, 272 eq. of HCN/h*Ni were then injected. After 30 min., the mixture took up no more HCN; a sample was taken from the reaction mixture and the following results were obtained by gas chromatography (GC percent by weight, internal standard: ethylbenzene):

| 4PN | MGN | AND | ADN selectivity (%) |
|-----|-----|-----|---------------------|
| 3.0 | 1.6 | 3.3 | 66.8 |

Example 21 (Inventive) (0.23 mmol of Ni(0))

1 eq. of NTP was admixed with 1000 eq. of 3PN and 2 eq. of ligand 4, stirred at 25° C. for one hour and heated to 60° C. 1 eq. of Et₃Al and 1 eq. of ZnCl₂ were added to this mixture and it was stirred for a further 5 min. In an Ar carrier gas stream, 298 eq. of HCN/h*Ni were then injected. After 100 min., the mixture took up no more HCN; a sample was taken from the reaction mixture and the following results were obtained by gas chromatography (GC percent by weight, internal standard: ethylbenzene):

| 4PN | MGN | AND | ADN selectivity (%) |
|-----|-----|-----|---------------------|
| 2.5 | 4.3 | 41.0 | 90.5 |

Example 22 (Comparative) (0.4 mmol of Ni(0))

1 eq. of NTP was admixed with 1000 eq. of 3PN and 3 eq. of ligand 5, stirred at 25° C. for one hour and heated to 70° C. 1 eq. of ZnCl₂ was added to this mixture and it was stirred for a further 5 min. In an Ar carrier gas stream, 337 eq. of HCN/h*Ni were then injected. After 150 min., the mixture took up no more HCN; a sample was taken from the reaction mixture and the following results were obtained by gas chromatography (GC percent by weight, internal standard: ethylbenzene):

| 4PN | MGN | ADN | ADN selectivity (%) |
|-----|-----|-----|---------------------|
| 0.7 | 4.7 | 72.4 | 94.0 |

Example 23 (Inventive) (0.4 mmol of Ni(0))

1 eq. of NTP was admixed with 1000 eq. of 3PN and 3 eq. of ligand 5, stirred at 25° C. for one hour and heated to 70° C. 1 eq. of Al(O-s-Bu)$_3$ and 1 eq. of ZnCl$_2$ were added to this mixture and it was stirred for a further 5 min. In an Ar carrier gas stream, 299 eq. of HCN/h*Ni were then injected. After 195 min., the mixture took up no more HCN; a sample was taken from the reaction mixture and the following results were obtained by gas chromatography (GC percent by weight, internal standard: ethylbenzene):

| 4PN | MGN | AND | ADN selectivity (%) |
|---|---|---|---|
| 0 | 4.9 | 90.9 | 94.7 |

Example 24 (Comparative): (0.4 mmol of Ni(0))

1 eq. of NTP was admixed with 1000 eq. of 3PN and 3 eq. of ligand 6, stirred at 25° C. for one hour and heated to 70° C. 1 eq. of ZnCl$_2$ was added to this mixture and it was stirred for a further 5 min. In an Ar carrier gas stream, 313 eq. of HCN/h*Ni were then injected. After 95 min., the mixture took up no more HCN; a sample was taken from the reaction mixture and the following results were obtained by gas chromatography (GC percent by weight, internal standard: ethylbenzene):

| 4PN | MGN | ADN | ADN selectivity (%) |
|---|---|---|---|
| 2.0 | 2.7 | 31.4 | 92.1 |

Example 25 (Inventive) (0.4 mmol of Ni(0))

1 eq. of NTP was admixed with 1000 eq. of 3PN and 3 eq. of ligand 6, stirred at 25° C. for one hour and heated to 70° C. 1 eq. of Al(O-s-Bu)$_3$ and 1 eq. of ZnCl$_2$ were added to this mixture and it was stirred for a further 5 min. In an Ar carrier gas stream, 303 eq. of HCN/h*Ni were then injected. After 130 min., the mixture took up no more HCN; a sample was taken from the reaction mixture and the following results were obtained by gas chromatography (GC percent by weight, internal standard: ethylbenzene):

| 4PN | MGN | AND | ADN selectivity (%) |
|---|---|---|---|
| 0 | 4.1 | 74.6 | 94.8 |

Example 26 (Comparative)

The procedure of example 14 was repeated with the difference that a mixture of 30 eq. of 4PN and 270 eq. of 3PN was used at the start. A sample was taken from the reaction mixture after 1, 2, 3, 4, 5 and 10 minutes and the content of 4PN was determined by gas chromatography (GC percent by weight, internal standard: ethylbenzene) to determine the influence on the reaction rate of the hydrocyanation to the ADN of the inventive additives and the following results were obtained:

| Min | 4PN | ADN |
|---|---|---|
| 1 | 3.4 | 4.1 |
| 2 | 3.4 | 5.7 |
| 3 | 3.3 | 7.4 |
| 4 | 3.4 | 10 |
| 5 | 3.4 | 12.1 |
| 10 | 3 | 24.5 |

Example 27 (Inventive)

The procedure of example 15 was repeated with the difference that a mixture of 30 eq. of 4PN and 270 eq. of 3PN was used at the start. A sample was taken from the reaction mixture after 1, 2, 3, 4, 5 and 10 minutes and the content of 4PN was determined by gas chromatography (GC percent by weight, internal standard: ethylbenzene) to determine the influence on the reaction rate of the hydrocyanation to give ADN of the inventive additives and the following results were obtained:

| Min | 4PN | ADN |
|---|---|---|
| 1 | 3.2 | 3.5 |
| 2 | 3.2 | 4.7 |
| 3 | 3.3 | 7.2 |
| 4 | 2.9 | 8.9 |
| 5 | 2.7 | 14.1 |
| 10 | 2.2 | 26.5 |

Comparative Overview

| | 4PN content [GC percent by weight] | |
|---|---|---|
| Time [min.] | Example 26 Without additive | Example 27 With Et$_3$Al |
| 1 | 3.4 | 3.2 |
| 2 | 3.4 | 3.2 |
| 3 | 3.3 | 3.3 |
| 4 | 3.4 | 2.9 |
| 5 | 3.4 | 2.7 |
| 10 | 3 | 2.2 |

The inventive additives thus do not exhibit any isomerization activity in the sense of U.S. Pat. No. 4,874,884 within the measurement accuracy.

| | ADN content [GC percent by weight] | |
|---|---|---|
| Time [min.] | Example 26 Without additive | Example 27 With Et$_3$Al |
| 1 | 4.1 | 3.5 |
| 2 | 5.7 | 4.7 |
| 3 | 7.4 | 7.2 |
| 4 | 10 | 8.9 |
| 5 | 12.1 | 14.1 |
| 10 | 24.5 | 26.5 |

The inventive additives thus do not exhibit any influence on the reaction rate of the hydrocyanation in the sense of U.S. Pat. No. 4,874,884 within the measurement accuracy.

We claim:

1. A system which is suitable as a catalyst for the hydrocyanation of olefinically unsaturated compounds and comprises;
   a) Ni(0),
   b) a compound which complexes Ni(0) as a ligand and comprises phosphites, phosphonites or mixtures thereof,
   c) a Lewis acid
   and
   d) a compound of the formula M $R_n$, where
   c) and d) are different, and
   where
   M is selected from Al or Ti,
   R is selected from identical or different monovalent alkoxy radicals, in which the alkoxy radicals may be bonded together, and if M=Al, R may also be identical or different monovalent alkyl radicals, in which the alkyl radicals may be bonded together or one or more alkyl radicals may be bonded to one or more of the abovementioned alkoxy radicals, and
   n is the valency of M.

2. The system according to claim 1, wherein R, is an alkoxy radical selected from the group consisting of, methoxy, ethoxy, 1-propoxy, 2-propoxy, 1-n-butoxy, 2-n-butoxy, 1-isobutoxy and 2-isobutoxy.

3. The system according to claim 1, wherein R is an alkyl radical, selected from the group consisting of methyl, ethyl, 1-propyl, 2-propyl, 1-n-butyl, 2-n-butyl, 1-isobutyl or 2-isobutyl.

4. The system according to claim 1, wherein compound d) is a titanium tetraalkoxide.

5. The system according to claim 1, wherein compound d) is an aluminum trialkoxide.

6. The system according to claim 1, wherein compound d) is a trialkylaluminum.

7. The system according to claim 1, wherein the R radicals in compound d) are the same.

8. A process for hydrocyanating an olefinically unsaturated compound comprising contacting the olefinically unsaturated compound with the catalyst system, according to claim 1.

9. The process according to claim 8, wherein the olefinically unsaturated compound comprises a functional group selected from the group consisting of —CN, —COOR$^1$, and —CONR$^2$R$^3$
   where R$^1$, R$^2$, R$^3$ are each independently the same or different, H or alkyl.

10. The process according to claim 8, wherein the olefinically unsaturated compound used is a compound of the formula ($C_4H_7$)—X
    where X is functional group selected from the group consisting of —CN, —COOR$^1$, and —CONR$^2$R$^3$
    where R$^1$, R$^2$, R$^3$ are each independently, the same or different, H or alkyl.

11. The process according to claim 8, wherein the olefinically unsaturated compound used is a linear pentenenitrile.

12. The process according to 8, wherein the olefinically unsaturated compound used is 3-pentenenitrile or 4-pentenenitrile.

13. The catalyst system of claim 1 wherein the zero-valent nickel complex comprises a ligand of formula I

P(X$^1$R$^1$)(X$^2$R$^2$)(X$^3$R$^3$)         I wherein X$^1$, X$^2$ and X$^3$ are each independently oxygen or a single band, and
    R$^1$, R$^2$ and R$^3$ are each independently alkyl radicals having from 1 to 10 carbon atoms or an aryl group.

14. The catalyst system of claim 13 wherein R$^1$, R$^2$ and R$^3$ are each independently selected from the group consisting of phenyl, o-tolyl, m-tolyl and p-tolyl.

* * * * *